(12) United States Patent
Tien et al.

(10) Patent No.: US 6,541,635 B1
(45) Date of Patent: Apr. 1, 2003

(54) METHOD FOR PRODUCING ANGIOTENSIN CONVERTING ENZYME INHIBITOR

(75) Inventors: Mong-Jong Tien, Taipei (TW); Yu-Liang Liu, Taipei (TW)

(73) Assignee: Everlight USA, Inc., Pineville, NC (US)

( * ) Notice: Subject to any disclaimer, the term of this patent is extended or adjusted under 35 U.S.C. 154(b) by 0 days.

(21) Appl. No.: 10/178,369

(22) Filed: Jun. 25, 2002

(30) Foreign Application Priority Data

Mar. 29, 2002 (TW) .......................... 91106399

(51) Int. Cl.[7] ...................... C07D 217/06; C07D 207/12
(52) U.S. Cl. .................... 546/147; 548/324.1; 548/409; 548/452; 548/533; 560/45
(58) Field of Search ...................... 546/147; 548/324.1, 548/409, 452, 533; 560/45

(56) References Cited

U.S. PATENT DOCUMENTS

| 5,359,086 A | 10/1994 | Merslavic et al. ........... 548/533 |
| 5,869,671 A | 2/1999 | Wang et al. ................. 546/147 |

FOREIGN PATENT DOCUMENTS

| CN | 1224004 | * 7/1999 | ......... C07D/207/16 |

* cited by examiner

Primary Examiner—Zinna Northington Davis
(74) Attorney, Agent, or Firm—Bacon & Thomas, PLLC

(57) ABSTRACT

The present invention discloses a method for producing angiotensin converting enzyme inhibitor of the following formula (I) and pharmaceutically acceptable salts thereof, in which a compound of the following formula (II),

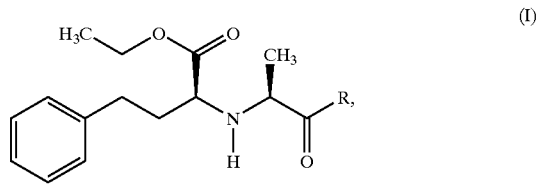

(I)

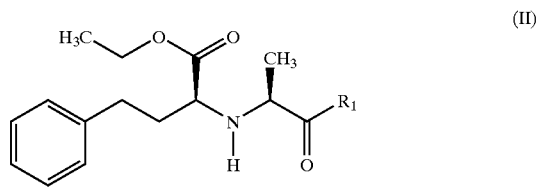

(II)

wherein R and $R_1$ are defined as in the specification, is subjected to a de-protective reaction of silyl group in non-aqueous medium. This reaction is easily carried out only in the non-aqueous medium, so that by-product is minimized and the yield is high.

19 Claims, No Drawings

METHOD FOR PRODUCING ANGIOTENSIN CONVERTING ENZYME INHIBITOR

BACKGROUND OF THE INVENTION

1. Field of the Invention

The present invention relates to a method for producing the derivatives of an inhibtor of Angiotensin Converting Enzyme.

2. Related Prior Art

Being an important medicine for hypertension, ACE inhibitor is significantly developed.

U.S. Pat. No. 4,716,235 mentioned a process for preparing Enalapril in aqueous phase. In this process, L-Proline was first dissolved in alkali aqueous solution to form an amino acid salt, which was then reacted with N-[1-(S)-ethoxycarbonyl-3-phenylpropyl]-L-alanine-N-carboxyanhydride (NEPA-NCA)/acetone to perform a Coupling Reaction. After NEPA-NCA was completely reacted, HCl(aq) was added to adjust the pH of the solution to 4.2. Next, acetone was removed by concentration, and the solution was extracted with a large amount of ethyl acetate three times, and dried with sodium sulfate. Unpurified Enalapril Maleate was finally obtained by filtration, concentration, being heated in acetonitrile, and mixing with maleic acid previously dissolved in heated acetonitrile.

U.S. Pat. No. 5,869,671 also mentioned a method for preparing Enalapril, in which silylated amino acid derived from L-Proline is first dissolved in an organic solvent and then reacted with NEPA-Acid chloride at a temperature lower than −10° C. After complete reaction, unpurified Enalapril Maleate can be obtained by adding water, adjusting pH to 3 with 3M HCl(aq), extracting with a large amount of dichloromethane three times, drying with sodium sulfate, filtering, concentrating and adding to maleic acid solution.

U.S. Pat. No. 5,359,086 mentioned another method for preparing Enalapril, in which L-Proline and chlorotrimethylsilane (TMSCl) were mixed to form a silylatedamino acid hydrochloric salt. Next, NEPA was dissolved in dichloromethane of −5° C. without organic alkali, and then N,N-carbonyldimidazole was added to perform a reaction at 0–5° C. for 3 hours. The above silylatedylated amino acid hydrochloric salt solution is then added to continue the reaction at 0–5° C. After the reaction is completed, dichloromethane is removed by vaporization, and water and ethyl acetate are added. The solution is then adjusted to pH 8.7 with 50% NaOH(aq), and extracted with ethyl acetate twice. The final product, unpurified Enalapril Maleate can be obtained by adding NaCl to aqueous phase to saturation, adding ethyl acetate, adjusting pH to 4.2 with 18% HCl(aq), extracting, drying with sodium sulfate, filtering, concentrating and adding maleic acid.

In these prior arts, acidic or alkaline aqueous reagents were used for reaction, and therefore more by-product were generated as shown in the following scheme (A). As a result, these processes had lower yield and more complicate operation was needed. Accordingly, the present invention provides an improved method to have higher yield.

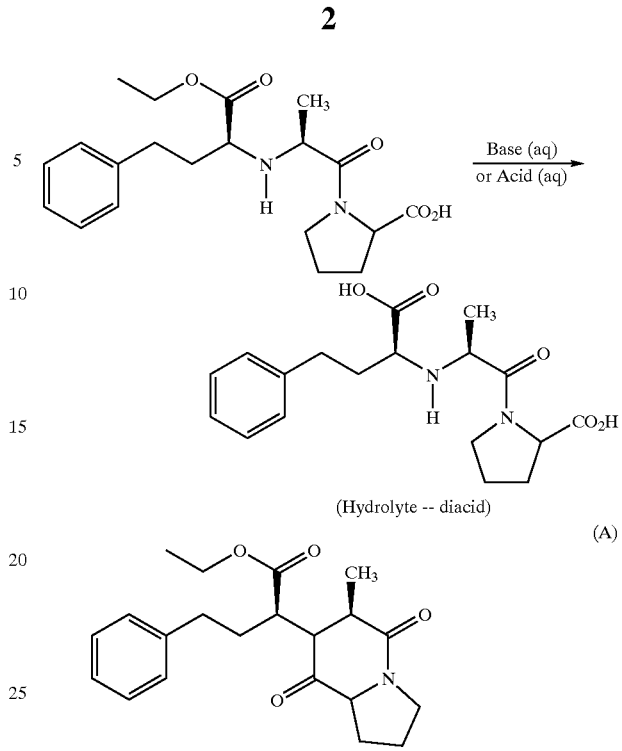

(A)

SUMMARY OF THE INVENTION

An object of the present invention is to provide a method for producing an angiotensin converting enzyme inhibitor, in which by-product is minimized and yield and purity are improved.

Another object of the present invention is to provide a method for producing an angiotensin converting enzyme inhibitor, which can be easily carried out and achieved in short time.

The method of the present invention includes steps of preparing a compound of the following formula (I) and pharmaceutically acceptable salts thereof, preferably hydrochloric salts and maleate, which is capable of inhibiting ACE.

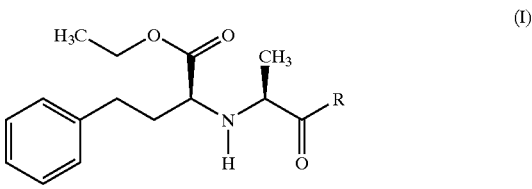

(I)

wherein R is selected from:

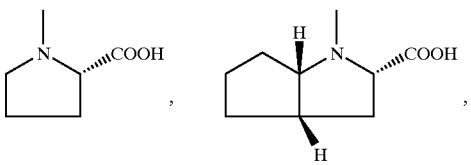

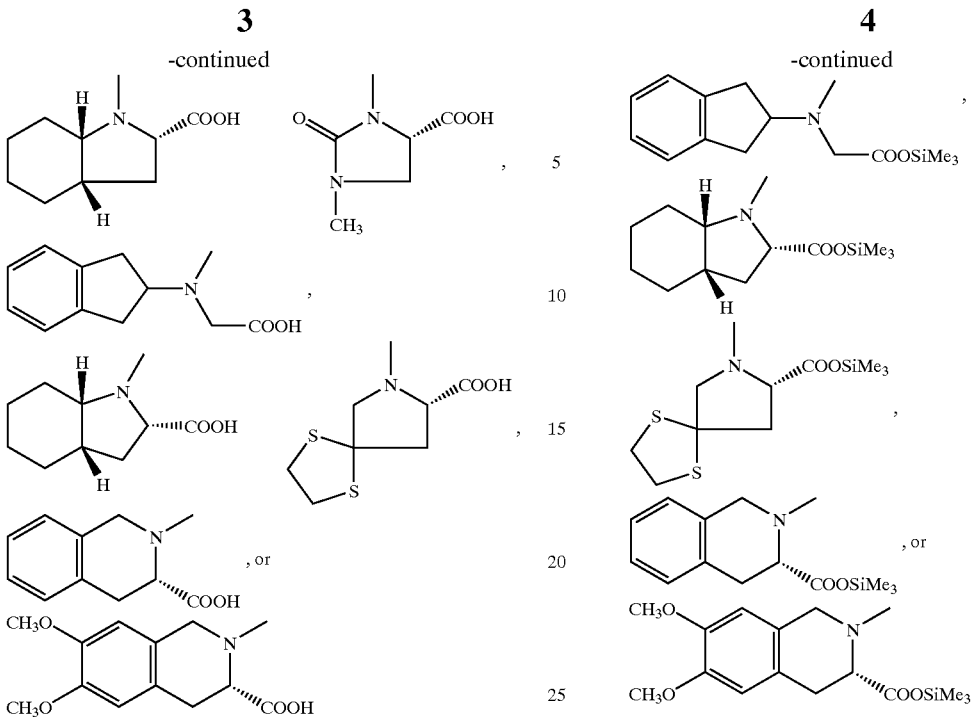

DETAILED DESCRIPTION OF THE INVENTION

In the present invention, a method for producing a compound of the formula (I) and pharmaceutically acceptable salts thereof primarily includes a de-protective reaction of silyl group of a compound of the following (II) in non-aqueous medium.

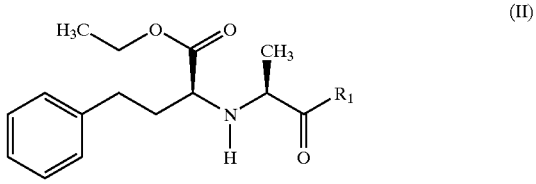

wherein $R_1$ is selected from:

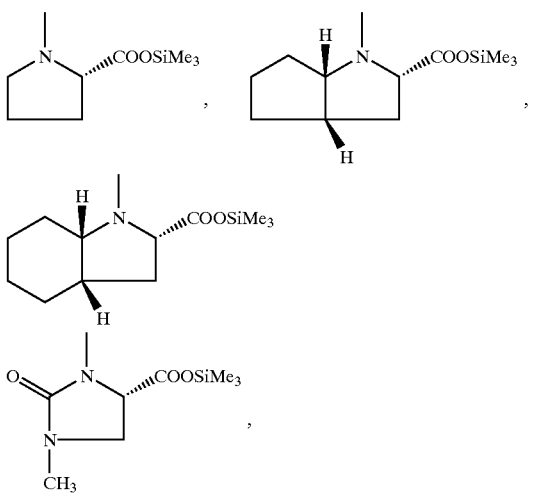

The non-aqueous medium aforementioned usually includes at least one organic solvent, which can be methanol, ethanol, 1-propanol, isopropanol, butanol, isobutanol, nbutanol, pentanol or butenediol.

The temperature for carrying out de-protective reaction of silyl group is not restricted, usually at 0° C.–60° C., and preferably at 5° C.–40° C.

The compound of the formula (II) can be obtained by reacting a compound of the following formula (III)

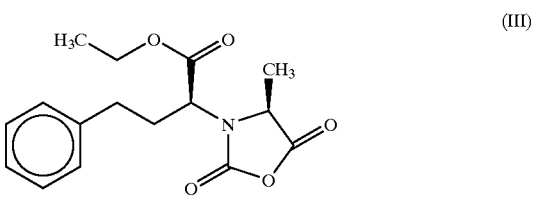

with a compound of the following formula (IV)

H—$R_1$                                                      (IV), wherein R1 is defined as the compound of the formula (II), in an aprotic solvent.

The aprotic solvent aforementioned usually includes at least one organic solvent, for example, butanedione, methyl ethyl ketone, acetonitrile, butyl nitrile, butyl dinitrile, ethyl ether, methyl ether, ethyl methyl ether, tetrahydrofuran, 1,4-dioxane, dichloromethane, dichloroethane, ethyl acetate or methyl acetate.

The temperature for producing the compound of the formula (II) is not restricted, and preferably at 20° C.–45° C.

The compound of the formula (III) used in the present invention can be referred to U.S. Pat. No. 6,262,274.

The compound of the formulae (IV) can be prepared by reacting an amino acid of the following formula (V)

H—R                                                           (V)

wherein R is defined as above, with a silylated compound in an aprotic solvent.

The amino acid of the formula (V) can be as the follows,

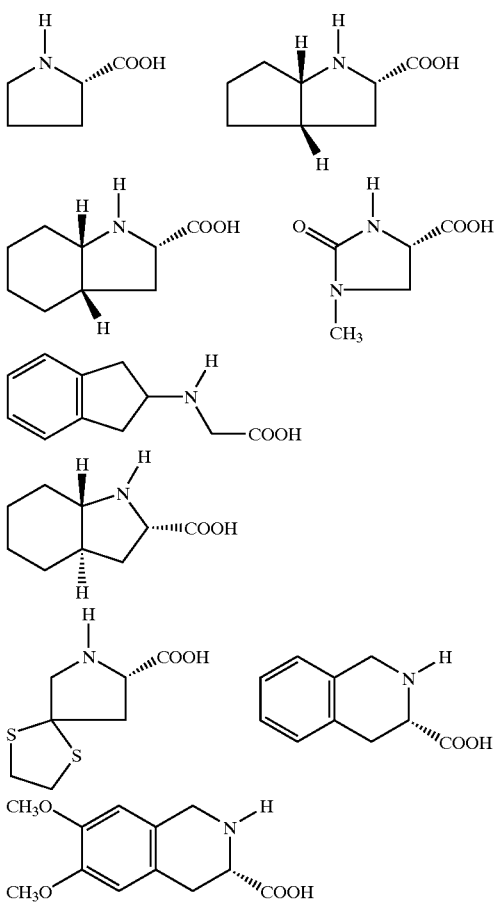

wherein L-Proline, (S)-1,2,3,4-Tetrahydro-3-isoquinolinecarboxylic acid and (S,S,S)-2-azabicyclo[3.3.0]octane-3-carboxylic acid are preferred.

The silylated compound can be. N,N'-bis(trimethylsily) urea (BSU), Hexamethylsilazanc (HMDS), chlorotrimethylsilane (TMSCl) or bis(trimethylsily)acetamide (BSA).

The aprotic solvent usually includes at least one organic solvent, for example, butanedione, methyl ethyl ketone, acetonitrile, butyl nitrile, butyl dinitrile, ethyl ether, methyl ether, ethyl methyl ether, tetrahydrofuran, 1,4-dioxane, dichloromethane, dichloroethane, ethyl acetate and methyl acetate.

The method for producing the compound of the formula (IV) can further include an organic alkali. For example, aliphatic amine can be added in a reaction of chlorotrimethylsilane and Proline to neutralize HCl generated during this reaction. The aliphatic amine can be methylamines, ethylamines such as triethylamine, phenylethylamine, diethylamine and deritatives thereof, propylamines, butanediamines, etc., wherein ethylamines are preferred.

The present invention characterizes in the one-pot reaction, that is, no separation procedure is necessary and the final pure product can be obtained in the only reactor. In such process, by-product is minimized and complicated purification is avoided.

DESCRIPTION OF THE PREFERRED EMBODIMENTS

The following examples are used to illustrate the present invention, but not to limit the scope thereof. In these examples, the percentage is counted by weight and the temperature is Celsius degree °C.

EXAMPLE 1

Synthesis of Enalapril

Step 1—Synthesis of Silylated Amino Acid

L-Proline (38.2 g), ethyl acetate (190 g) and chlorotrimethylsilane (TMSCl, 39.0 g) are added in a reactor and stirred at room temperature for 0.5 hour. Next, triethylamine (42.6 g) is added into the solution and stirred to obtain the silylated amino acid of the following formula (IV-1).

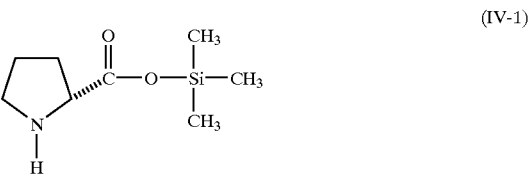

(IV-1)

Step 2—Coupling Reaction

NEPA-NCA (91.5 g) is dissolved in ethyl acetate (183 g), which is then added into the silylated amino acid solution of Step 1 and stirred at room temperature until NEPA-NCA was reacted completely. Consequently, NEPA silylated amino acidified intermediate of the following formula (IV-2) is obtained.

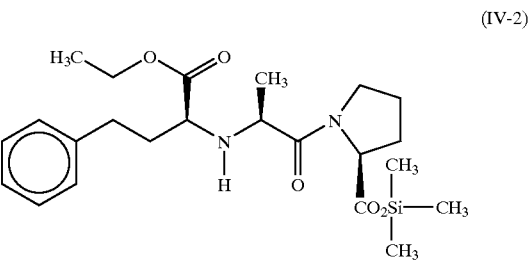

(IV-2)

Step 3—De-protective Reaction of Silyl Group

The solution of NEPA silylated amino acidified intermediate is first filtered to remove amino salts, and then iso-propanol (27 g) is added and stirred at room temperature to obtain N-[1-(S)-ethoxycarbonyl-3-phenylpropyl]-L-alanyl-L-proline (Enalapril), which has the ability for inhibiting ACE and is a SSS stereo compound of the following formula (VI).

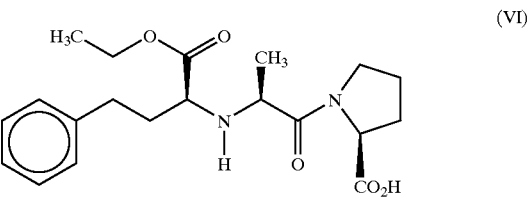

(VI)

Step 4—Complex Reaction

The Enalapril of Step 3 is concentrated, and iso-propanol (200 g) is then added therein. Next, maleic acid (40.2 g) is dissolved in iso-propanol (201 g), which is then added into the above solution under water bath at 60° C., and then the temperature of water bath is elevated to 75° C. After clarified, the mixture is cooled down to obtain a white precipitate, which is then filtered to obtain final product (128.7 g) of the following formula (VII), N-[1-(S)-ethoxycarbonyl-3-phenylpropyl]-L-alanyl-L- proline.maleate (Enalapril Maleate). The yield is 87.1%.

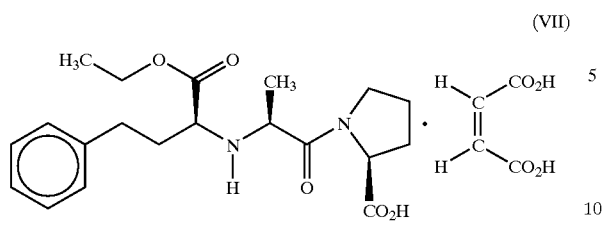

(VII)

$^1$HNMR(D$_2$O) δ 1.30(t,3H); 1.54,1.59(d,3H); 1.80,195, 2.00(m,2H); 2.02,2.23,2.25(m,2H); 2.29(m,2H); 2.80(m, 2H); 3.45,3.58(m,2H); 3.95,4.41(t,dd,1H); 4.09,4.29(q,1H); 4.26(q,2H); 6.33(s,2H); 7.31(m,3H); 7.39(t,2H)

$^{13}$CNMR 16.15; (17.43,17.90); (24.93,27.47); (31.80, 33.98); 33.16; (33.90,34.38); (50.30,50.37); (57.88,58.31); (61.49,61.68); (63.28,63.64); 66.90; (129.70,129.75); 131.56; 131.80; 136.98; (142.55,142.66); (170.27,170.98); (172.02,172.17); 173.62; (179.17,179.25)

EXAMPLE 2

Synthesis of Quinapril

Step 1—Synthesis of Silylated Amino Acid (S)-1,2,3,4-tetrahydro-3-isoquinolinecarboxylic acid (17.7 g), dichloromethane (88.5 g) and bis(trimethylsily) acetamide (BSA, 24.5. g) are added into a reactor and stirred at room temperature until the mixture is clarified to obtain silylated amino acid of the following formula (IX).

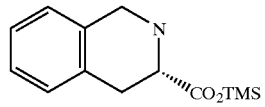

(IX)

Step 2—Coupling Reaction

NEPA-NCA (27.9 g) is dissolved in dichloromethane (60 g), and then mixed in the silylated amino acid solution of Step 1, which is then heated in water bath at 40–45° C. and stirred with circulation until NEPA-NCA is completely reacted. Finally, a NEPA-NCA silylated amino acidified intermediate of the following formula (X) can be obtained.

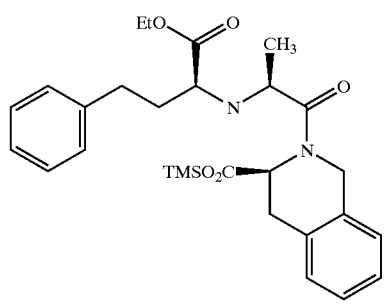

(X)

Step 3—De-protective Reaction of Silyl Group

Isopropanol (12 g) is added into the above solution of NEPA-silylated amino acidified intermediate and stirred at 5–10° C., which is then filtered to remove excessive amino acid. By comparing with HPLC spectrum of the standard sample (HPLC, 90%), the final product 2-[2-[(1-(ethoxycarbonyl)-3-phenylpropyl)amino-1-oxopropyl]-1,2, 3,4-tetrahydro-3-isoquinoline carboxylic acid (Quinapril) capable of inhibiting ACE, which is a SSS stereo compound and has the following formula (XI).

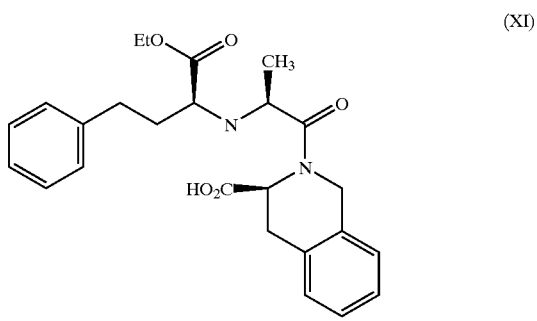

(XI)

Step 4—Complex Reaction

The above Quinapril solution is allowed to perform a complex reaction with HCl and then a white precipitate is obtained. After filtering and recrystalizing the precipitate with THF/acetonitrile, 2[2-[1-[ethoxycarbonyl-3-phenylpropyl]-1-aminopropanoyl]-1,2,3,4-tetrahydro-3-iso-quinolylic acidhydrochloric acid (Quinapril.HCl) of the following formula (XII) can be obtained. mp=119–121.5° C.; $[α]_D^{25}$ +15.4° (concentration=2, dissolved in methanol).

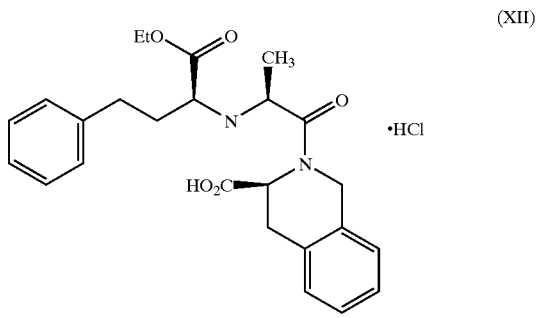

(XII)

$^1$HNMR(Me$_2$SO-d$_6$) δ 1.25(t,3H); 1.53(d,3H); 2.22(t, 2H); 2.70(m, 2H); 3.20(m, H-4); 3.85(m,1H); 4.20(m, 1H); 4.20(q, 2H); 4.40–4.50(m, 2H); 7.20(m, 9H)

EXAMPLE 3

Synthesis of Ramipril

Repeat steps of Example 1, wherein the amino acid compound is replaced with (S,S,S)-2-azabicyclo[3.3.0] ctane-3-carboxylic acid of the following formula (XIII), $[α]_D^{24}$ +33.2° (concentration=1, dissolved in 0.1N HCl-ethanol). (2,S,3aS,6aS)-1[(S)-2[(S)-1-[ethoxycarbonyl-3-phenylpropyl]amino propanoyl]octahydrocyclopenta[6] pyrrole-2-carboxylic acid (Ramipril) of the following formula (XIV) is obtained.

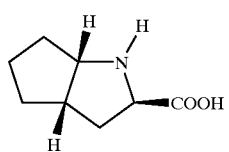

(XIII)

-continued

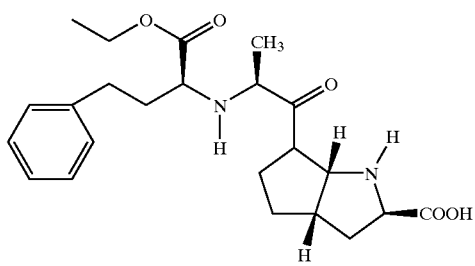

(XIV)

The present invention provides a method for producing the angiotensin converting enzyme inhibitor, which exhibits the characters of easy operation, saving time, less by-product and higher yield. Additionally, for one-pot reaction in an organic solvent without water, the by-product is less and can be removed more easily, whereby the pure final product can be obtained directly.

From the foregoing description, one skilled in the art can easily ascertain the essential characteristics of this invention, and without departing from the scope thereof, can make various changes and modifications of the invention to adapt it to various usages and conditions. Thus, other embodiments are also within the claims.

What is claimed is:

1. A method for producing a compound of the following formula (I) and pharmaceutically acceptable salts thereof,

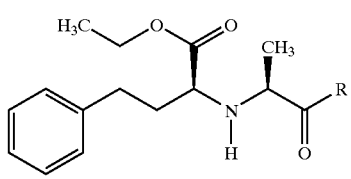

(I)

wherein R is

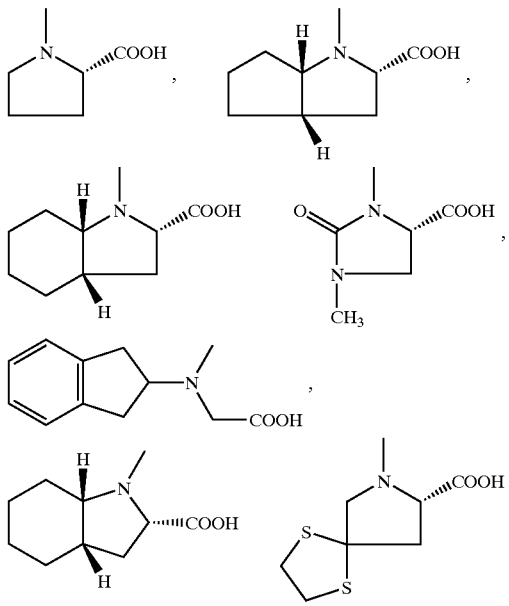

-continued

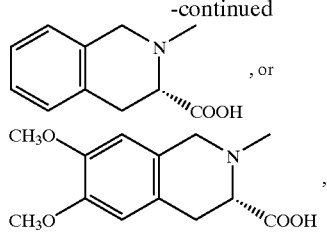

comprising a de-protective reaction of silyl group of a compound of the following (II) in a non-aqueous medium:

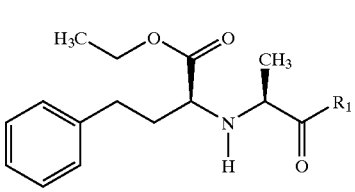

(II)

wherein $R_1$ is

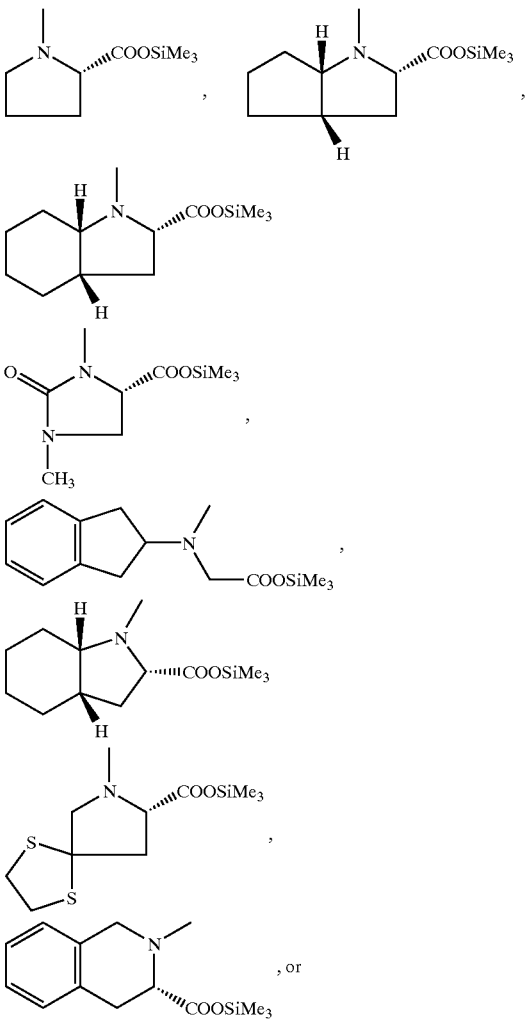

[Structure: tetrahydroisoquinoline with CH3O groups and COOSiMe3 substituent]

2. The method of claim 1, wherein said non-aqueous medium comprises at least one organic solvent.

3. The method of claim 2, wherein said organic solvent is selected from the group consisting of methanol, ethanol, 1-propanol, isopropanol, butanol, isobutanol, n-butanol, pentanol and butenediol.

4. The method of claim 2, wherein said organic solvent is iso-propanol.

5. The method of claim 1, wherein said de-protective reaction is carried out at a temperature of 5° C. to 40° C.

6. The method of claim 1, wherein said compound of the formula (II) is prepared by reacting a compound of the following formula (III)

(III)

with a compound of the following formula (IV)

H—R$_1$    (IV), wherein R$_1$ is defined as claim 1, in an aprotic solvent.

7. The method of claim 6, wherein said aprotic solvent comprises at least one organic solvent.

8. The method of claim 7, wherein said aprotic solvent is selected from the group consisting of butanedione, methyl ethyl ketone, acetonitrile, butyl nitrile, butyl dinitrile, ethyl ether, methyl ether, ethyl methyl ether, tetrahydrofuran, 1,4-dioxane, dichloromethane, dichloroethane, ethyl acetate and methyl acetate.

9. The method of claim 6, wherein said compounds of the formulae (III) and (IV) are reacted at a temperature of 20° C. to 45° C.

10. The method of claim 6, wherein said compound of the formulae (IV) is prepared by reacting an amino acid of the following formula (V),

H—R    (V)

wherein R is defined as claim 1, with a silylated compound in an aprotic solvent.

11. The method of claim 6, wherein said silylated compound is selected from the group consisting of N,N'-bis(trimethylsily)urea (BSU), Hexamethylsilazanc (HMDS), chlorotrimethylsilane (TMSCl) and bis(trimethylsily)acetamide (BSA).

12. The method of claim 10, wherein said aprotic solvent comprises at least one organic solvent.

13. The method of claim 12, wherein said organic solvent is selected from the group consisting of butanedione, methyl ethyl ketone, acetonitrile, butyl nitrile, butyl dinitrile, ethyl ether, methyl ether, ethyl methyl ether, tetrahydrofuran, 1,4-dioxane, dichloromethane, dichloroethane, ethyl acetate and methyl acetate.

14. The method of claim 10, which further comprises an organic alkali.

15. The method of claim 14, wherein said organic alkali is aliphatic amine.

16. The method of claim 1, wherein said pharmaceutically acceptable salts are hydrochloric salts or maleates.

17. The method of claim 10, wherein said amino acid is selected from L-Proline, (S)-1,2,3,4-Tetrahydro-3-isoquinolinecarboxylic acid or (S,S,S)-2-azabicyclo[3.3.0]octane-3-carboxylic acid.

18. The method of claim 1, wherein said compound of the formula (I) is one of compounds of the following formulae (VI), (XI) and (XIV), (VI)

(XI)

(XIV)

19. A method for producing N-[1-(S)-ethoxycarbonyl-3-phenylpropyl]-L-alanyl-L-proline maleate (Enalapril Maleate) of the following formula (VII), (VII)

comprising a step of mixing the compound of the formula (VI) as claimed in claim 18 with maleic acid.

* * * * *